(12) United States Patent
Dunham et al.

(10) Patent No.: US 6,741,671 B2
(45) Date of Patent: May 25, 2004

(54) COMPUTED TOMOGRAPHY SYSTEM WITH INTEGRATED ANALOGIC COMPUTER

(75) Inventors: Bruce Matthew Dunham, Mequon, WI (US); John Scott Price, Wauwatosa, WI (US); Carey S. Rogers, Waukasha, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 109 days.

(21) Appl. No.: 10/063,496

(22) Filed: Apr. 30, 2002

(65) Prior Publication Data
US 2003/0202629 A1 Oct. 30, 2003

(51) Int. Cl.[7] .................................................. A61B 6/00
(52) U.S. Cl. ............................. 378/4; 378/19; 378/98.8
(58) Field of Search ................................ 378/4, 19, 21, 378/62, 98.8, 901; 382/131

(56) References Cited
U.S. PATENT DOCUMENTS 6,285,902 B1 * 9/2001 Kienzle et al. ............. 600/427
6,600,803 B2 * 7/2003 Bruder et al. ................. 378/19

* cited by examiner

Primary Examiner—Edward J. Glick
Assistant Examiner—Courtney Thomas
(74) Attorney, Agent, or Firm—Peter Vogel

(57) ABSTRACT

An imaging system includes an x-ray source adapted to generate an x-ray flux. The system further includes an array of analogic computer modules, each of which contains an array of detector elements arranged to form "slices" as in a CT scanner. The analogic computer modules then process the signals from the detector elements.

14 Claims, 5 Drawing Sheets

US 6,741,671 B2

COMPUTED TOMOGRAPHY SYSTEM WITH INTEGRATED ANALOGIC COMPUTER

BACKGROUND OF INVENTION

The present invention relates generally to imaging systems and more particularly to computed tomography.

A computed tomography or CT scan is a method of taking pictures of the inside of the body using an ultra-thin x-ray beam. As the x-ray beam passes through the body, it is absorbed by bones, tissues and fluid within the body, thereby varying resultant beam intensity. The intensity of the attenuated x-ray beam emerging from the body is measured by a device that converts x-ray beam photons into electrical signals. These signals are converted into a detailed picture.

Multi-slice CT scanners are special CT systems equipped with a multiple-row detector array rather than a single-row detector array. This allows for simultaneous scan of multiple slices at different locations.

A typical CT scanner includes a gantry having an annular frame for rotatably supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a beam of energy, or x-rays, along a scan plane, through the patient, and to the detector array. By rotating the x-ray source about the scanning axis and relative to the patient, x-rays are projected through the patient from many different directions. An image of the scanned portion of the patient is then reconstructed from data provided by the detector array using a scanner computer.

Cellular neural networks (CNN) are multi-dimensional lattice arrays of pluralities of substantially identical cells. For two-dimensional (2D) planar arrays of cells, the arrays are typically square, rectangular, or hexagonal.

With respect to any single cell, the cells closest to it are neighbor cells. The neighbor cells of each cell expand concentrically outward from that cell in partial concentric circles of neighbor cells. Each cell in the array interacts in a non-linear fashion and in continuous time with a prescribed number of concentric circles of neighbor cells within a lattice. Adjacent cells interact directly with each other, and cells not directly connected together may affect each other indirectly because of the propagation effects of the CNN.

In current CT systems, the detector, data acquisition system and processing computer are separate components. The low-level signals are pre-amplified, sent to an analog-to-digital converter and then passed to the processing unit. A primary disadvantage of the aforementioned system is the required signal cables and connections that add to system noise.

A further disadvantage of the aforementioned system is that the data acquisition system (DAS) is cumbersome and increases in complexity as more slices are added to the system.

The disadvantages associated with current, CT systems have made it apparent that a new technique for CT scanning and data transfer is needed. The new technique should substantially increase data transfer speeds from the detectors to the computer display while substantially reducing system noise and should also decrease size and weight of CT systems. The present invention is directed to these ends.

SUMMARY OF INVENTION

In accordance with one aspect of the present invention, an imaging system includes an x-ray source adapted to generate an x-ray flux. The system further includes a first module comprising a first detector array, the first module adapted to generate a first module signal in response to the x-ray flux; and a host computer adapted to receive the first module signal, the host computer further adapted to activate the x-ray source in response to the first module signal.

In accordance with another aspect of the present invention, a method for data collection for an imaging system comprising: activating an x-ray source; generating an x-ray flux; receiving said x-ray flux in at least one analogic computer module comprising a detector array; generating a module signal in response to said x-ray flux; and receiving said module signal in a host computer.

One advantage of the present invention is that it substantially eliminates long signal cables and connections. Another advantage is that low-level signals originating at the detector elements are processed without further amplification or transmission.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

Figure 1:
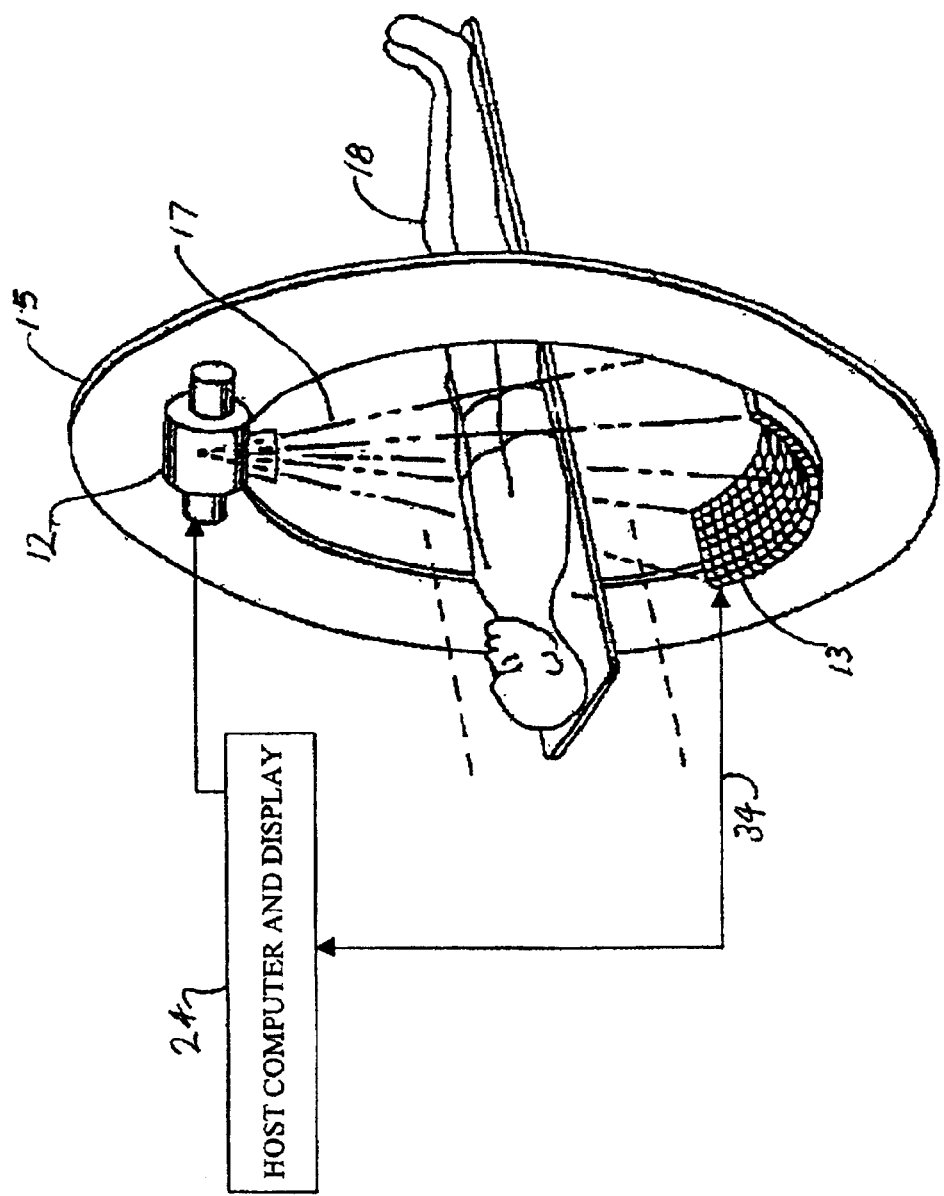
FIG. 1 is a diagram of a CT scanning system, in accordance with a preferred embodiment of the present invention.

_Hlk526158799 The present invention is illustrated with respect to a Computed Tomography (CT) scanning system 10, particularly suited to the medical field. The present invention is, however, applicable to various other uses that may require CT scanning, as will be understood by one skilled in the art. _Hlk526158799 Referring to FIGS. 1, 2 and 3, a diagram of a CT scanning system 10 including an x-ray source 12 generating an x-ray flux 17, in accordance with a preferred embodiment of the present invention, is illustrated. The system 10 further includes a CT detector 13 (here embodied as a curved mount tug plate) having a first analogic computer module 14. The first analogic computer module 14 includes a first detector array 16 and generates a first module signal in response to the x-ray flux 17, which passes an object 18 (e.g. a patient). A second analogic computer module 20 includes a second detector array 22. The second analogic computer module 20 electrically communicates with the first analogic computer module 14 and generates a second module signal in response to the x-ray flux 17. The detector arrays are similar to cellular neural networks (CNNs), as will be understood by one skilled in the art. A host computer 24 (host computer and display) receives the first module signal and the second module signal and activates the x-ray source 12.

The x-ray source 12 is embodied as a flat panel x-ray source or an extended x-ray source (e.g. Imatron), or a standard x-ray tube. The x-ray source 12 is activated by either the host computer 24 or through an x-ray controller 25, as will be understood by one skilled in the art. The x-ray source is ideally coupled to a gantry 15 controlled through a gantry control unit 19, which is controlled through the host computer 24. The x-ray source 12 sends the x-ray flux 17 through an object 18 on a moveable table 27 controlled by a table control device 29 acting in response to from the host computer 24, as will be understood by one skilled in the art.

The present invention is illustrated with respect to CT, however it is alternately used for any type of x-ray system using a detector including mammography, vascular x-ray imaging, bone scanning, etc. Further embodiments include non-medical applications such as weld inspection, metal inspection. Essentially, anything that could use a digital x-ray detector to make 1, 2 or 3 dimensional images.

Figure 2:
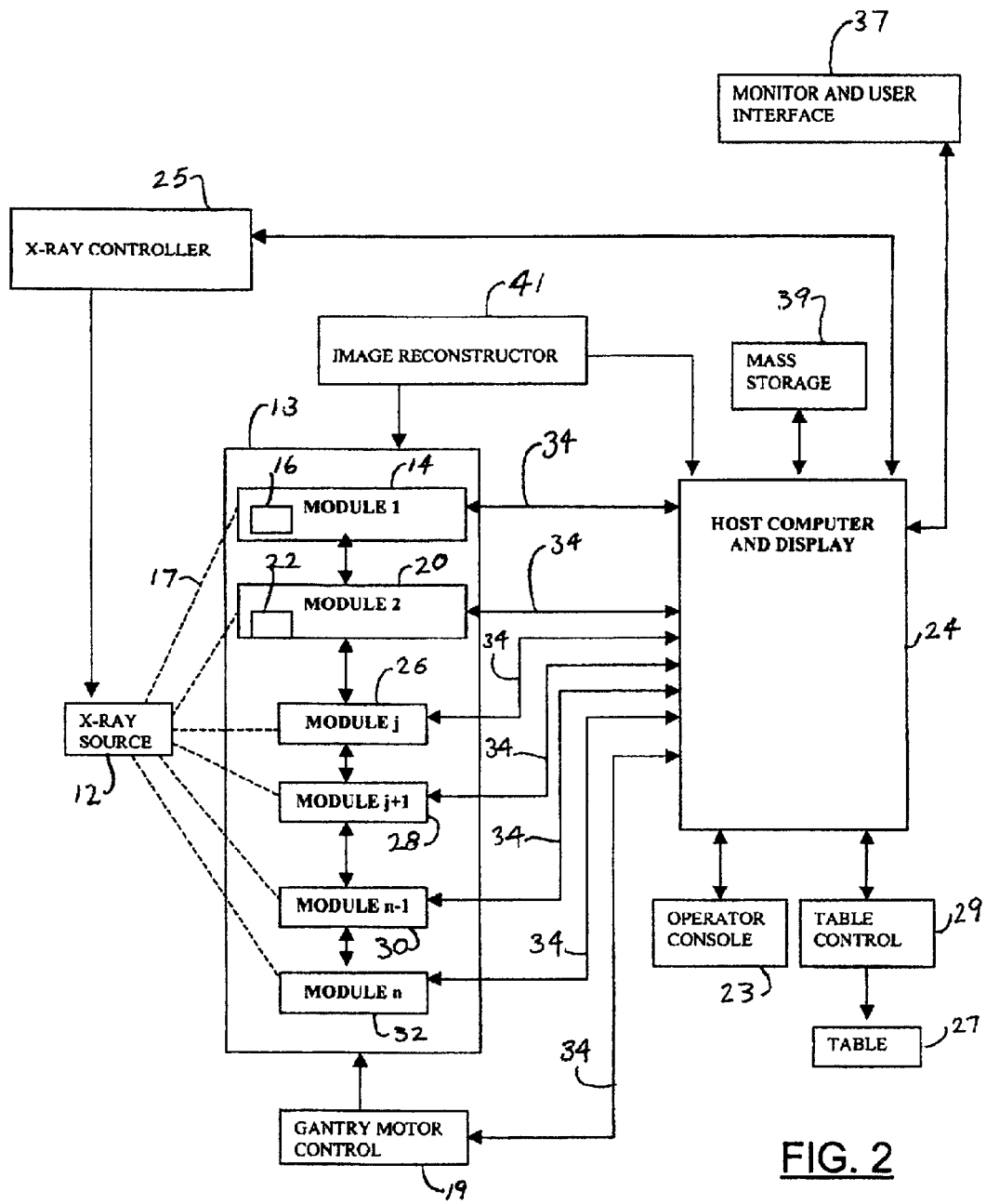
FIG. 2 is a component diagram illustrating communication between the host computer and the analogic computer modules of FIG. 1.

For a full CT detector 13, numerous analogic computer modules are arranged linearly as shown in FIG. 2 on the curved mount tug plate from FIG. 1. As one skilled in the art will recognize, the first and second analogic computer modules 14, 20, a j module 26, a j+1 module 28, an n−1 module 30 and an n module 32 are illustrated. The j module 26 is a module number greater than two, and the n module 32 is the highest numbered analogic computer module. Each analogic computer module shares information with other modules and has input/output (I/O) lines 34 to the host computer and display units 24. Such a system 10 substantially eliminates the need for bulky data-acquisition systems used on current CT machines, and substantially eliminates long signal cables and connections. Particularly, low-level signals originating at the detector elements are processed without further amplification or transmission, thereby reducing system noise.

The first analogic computer module 14 includes a first detector array 16 and generates a first module signal in response to the x-ray flux 17. The first analogic computer module 14 ideally includes a memory unit 38 storing intermediate stages of an image generation cycle from the first detector array 16 and a communication unit 40 sending and receiving signals from the host computer 24. The first analogic computer module 14 electrically communicates with other analogic computer modules 20, 26, 28, 30, and 32, as was previously discussed. Each computer module is an analogic computer, the host computer 24 collects the image data from the modules, displays it, and provide communication paths between the modules.

The second analogic computer module 20 includes a second detector array 22, electrically communicates with the first analogic computer module 14, and generates a second module signal in response to the x-ray flux 17.

Figure 3:
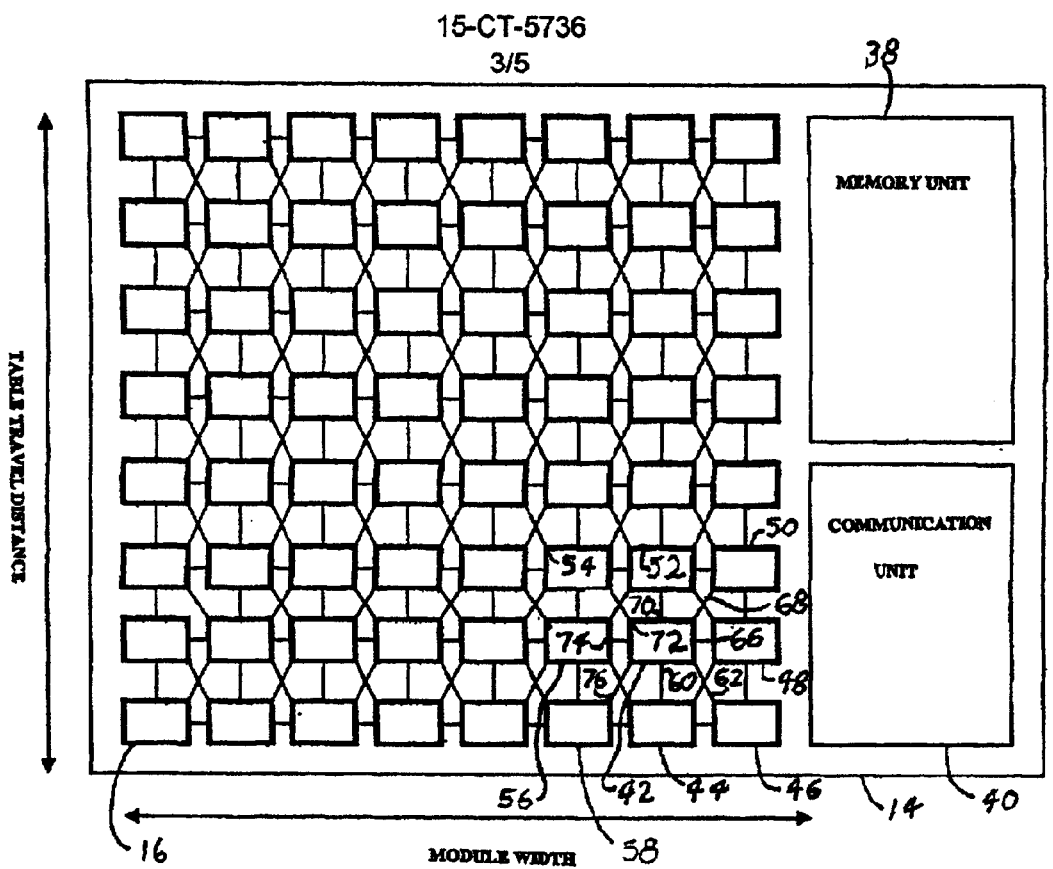
FIG. 3 is a schematic diagram of an analogic computer module from FIGS. 1 and 2.

There are sixty-four detector elements each shown schematically in FIG. 3 as interconnected to the nearest neighbors, i.e., the first layer of neighbor detector elements. For example, element 42 is shown interconnected with elements 44, 46, 48, 50, 52, 54, 56, and 58 by links 60, 62, 66, 68, 70, 72, 74, and 76 respectively. Each of links 60, 62, 66, 68, 70, 72, 74, and 76 are bi-directional between the two elements to which that link is connected. In this example, there is only one layer of neighbor interconnects between the elements with elements 44, 46, 48, 50, 52, 54, 56, and 58 substantially forming a circle around element 42. The 64 detectors are arranged in an 8×8 array. The individual rows of 8 are combined with the collinear rows of 8 in the other modules to make up a slice as was previously mentioned. The 8×8 array (64 elements) is only an example, the array is alternately enlarged for an increased number of slices. A further example is an 12×256 array, which could be used for a 256 slice system.

Each detector element communicates with the nearest neighbors to facilitate filtering and smoothing operations required for image processing. An alternate embodiment includes each detector element communicating with each other detector element, as will be understood by one skilled in the art. Intermediate stages of image generation can be stored in memory unit 38 and input/output (I/O) sections (communication unit 40), which are supplied for communication with the outside world, as will be understood by one skilled in the art.

The individual detector elements are arranged in a module, such as the first analogic computer module 14, as shown in FIG. 2. Modern CT detectors typically have N-slices in the table motion direction, where N is 4, 8, 16, or other number depending on system requirements. These multi-slice configurations extend area of coverage and offer reduced scan times and increased resolution. The analogic sensory computer module is also arranged in this manner. The size of the elements (e.g. element 42) is typically between 0.5 and 1.0 mm. The detector elements are embodied as GE Lumex or any other x-ray sensitive detection elements.

The host computer 24 receives the first module signal and the second module signal. The host computer 24 also activates the x-ray source 12, however, alternate embodiments include independent activation means for the x-ray source. The present invention includes an operator console 23 for control by technicians, as will be understood by one skilled in the art.

The system 10 is based on analogic computers, and the data is presented in analog form, so analog-to-digital conversion is unnecessary. This implementation tends to reduce weight and complexity, and thereby decreases computation time, as will be understood by one skilled in the art.

The computing is based on a cellular neural network (CNN) which consists of a regular grid of identical dynamical systems with mostly local connections and an interconnection pattern or cloning template. The connections and templates are loaded into the system 10 for a particular application. For the embodied host computer 24, the dynamical system 10 is treated continuously except for the discrete nature of the detector elements (e.g. element 42).

Since the data is acquired and processed in real time, the scout image, for example, is presented to a radiology technician through the monitor and user interface 37 while the scan is occurring. The host computer 24 needs only read pixels values from each module and update the display at the appropriate locations through, for example, an image reconstructor 41. The host computer 24 alternately stores image data in a mass storage unit 39 for future reference.

An alternate embodiment incorporates a similar analogic computer in a flat panel x-ray source, such as the GE Senographe 2000D Full Field Digital Mammography System. A Flat panel x-ray source using analogic computer elements also benefits from the reduced noise due to the elimination of the analog to digital conversion step. The neural networks are easily reprogrammed for different tasks and to account for the variations in detection and x-ray emission processes.

One embodiment of the present invention incorporates use of x-ray analogic computer modules for the scout scan on a CT system. During a scout scan from the x-ray source to the detector elements, the x-ray tube remains stationary while the patient table translates under the x-ray flux 17. This results in a two-dimensional image ideal for qualitative information and for locating the desired position for scanning during further CT exams.

An alternate embodiment includes analogic sensory computer system in conjunction with and extended source CT system as part of an image guided surgery technique. In addition, a standard x-ray tube can be used by rotating the gantry and pulsing the x-ray tube to locate the catheter.

Figure 4:
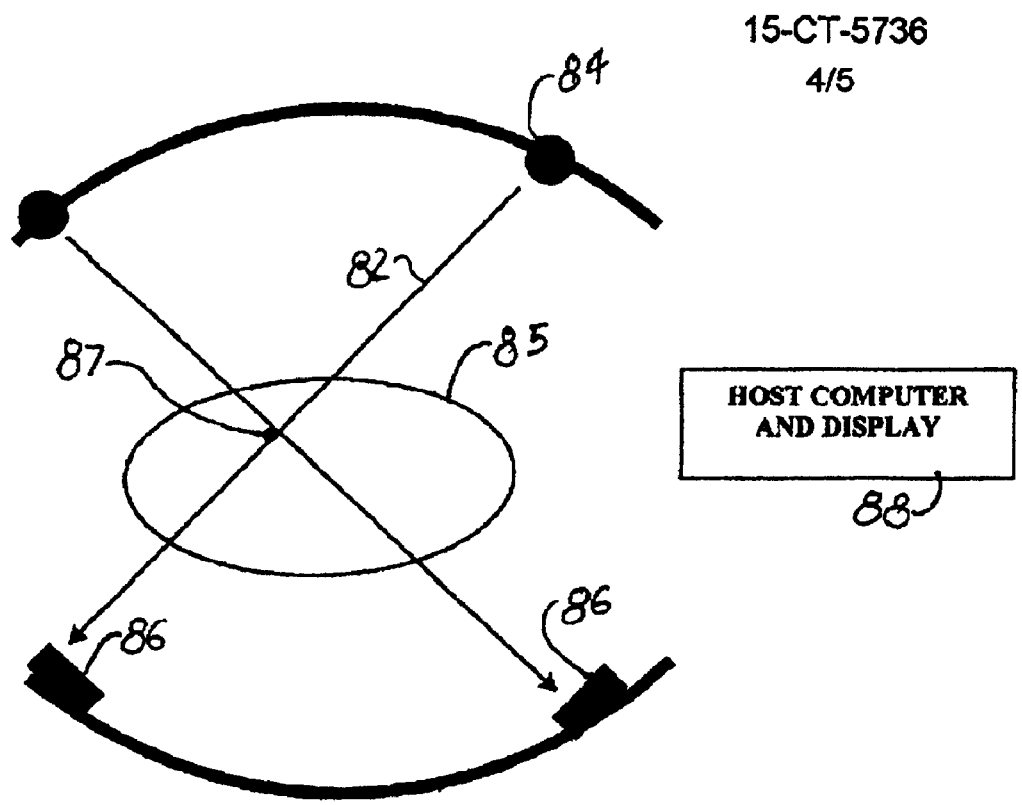
FIG. 4 is an alternate embodiment of FIG. 1.

Referring to FIG. 4, an alternate embodiment of the present invention includes tracking a catheter 80 or other probe during surgical procedures. For example, before an exam, a full helical or axial CT scan is performed to generate a three-dimensional (3D) image of the part of the body under examination. Once the exam begins, very low dose bursts of x-rays 82 are emitted from alternate ends of the extended x-ray source 84 through the object 85 under study and detected by the analogic detectors 86. The neural network is programmed to track the location of the probe 87 and send that information back to the host computer 88 where it is displayed on the 3D image in real-time for the doctor to view. The information can also be fed back to a robotic control system for position the probe or instrument to provide real-time control and positioning.

The combination of the analogic computer modules and host computer 88 with an extended x-ray source provides the location of the probe in real time and at a much-reduced dose than was previously available.

Figure 5:
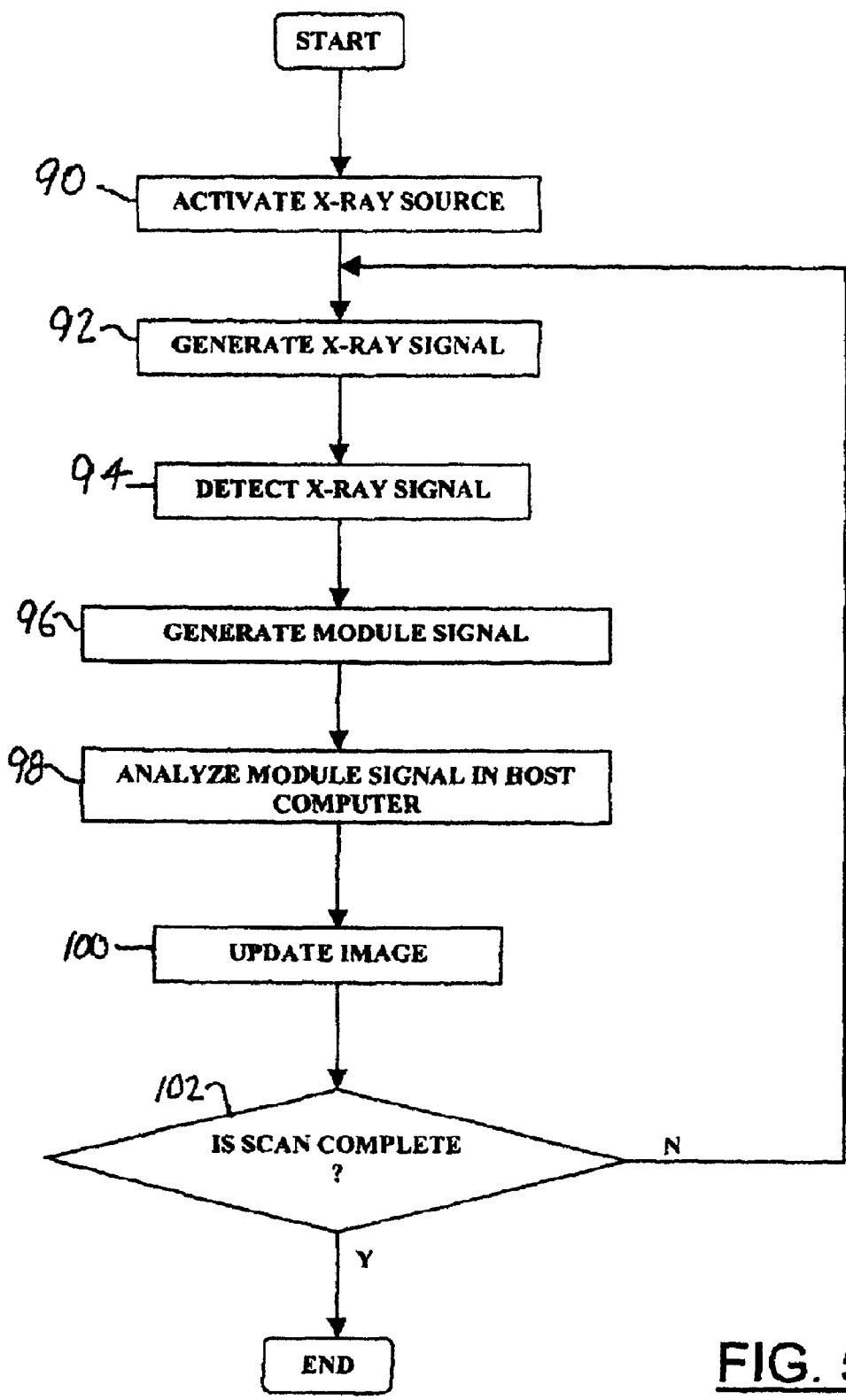
FIG. 5 is a block diagram of a method for scanning an object, in accordance with a preferred embodiment of the present invention.

Referring to FIG. 5, a block diagram of a Computed Tomography (CT) scanning system is illustrated. Logic starts in operation block 90 where the x-ray source is activated by the host computer. Subsequently, in operation block 92, the x-ray source generates an x-ray flux, which typically travels through a patient.

Operation block 94 then activates, and the analogic computer modules detect the x-ray flux and generate at least one module signal, in operation block 96, in response to the x-ray flux. Operation block 98 then activates, and the host computer analyzes the module signals, and updates the resultant scan image in operation block 100.

A check is then made in inquiry block 102 whether the scan is complete. For a positive response, the host computer stops scanning. Otherwise, operation block 92 reactivates and blocks 94, 96, 98, 100 and 102 subsequently activate in turn.

In operation, the method for data collection for an imaging system includes the steps of activating an x-ray source, thereby generating an x-ray flux. Following reception of the x-ray flux in at least one analogic computer module including a detector array, a module signal is generated and subsequently received in a host computer.

The host computer cycles typical image processing steps in response to the module signal, as will be understood by one skilled in the art. In other words, data offsets are corrected and x-ray dosage is measured and the raw data is normalized to the dose in real-time. Necessary calibration corrections are made, and the resulting signal is filtered, typically through a low dose filter and an adaptive filter, to reduce noise in the signal. The signal is then converted to display pixel format and subsequently displayed.

FIG. 1 illustrates the processing steps for one pixel of an analogic computer module. An x-ray flux 17 from the x-ray source 12 passes through the patient and impinges on the x-ray detector 13. The signal 17 passes directly to the analog computer modules, where the signal is converted to a gray level corresponding to the attenuation of the x-ray photon through the patient, for the final scout image.

A new method for data collection and processing applied to medical imaging is disclosed. Recent advances in computing technology allow the direct integration of analog detectors and computers without the analog-to-digital conversion used in all present systems. In these analog computers, the sensor is a component of the computer, not a separate entity. Previously, all work done with sensory computing has been in the field of image analysis and remote sensing at optical wavelengths. Whereby optical sensors are integrated with the analog computers, real-time processing on the order of teraflops is potentially achieved.

From the foregoing, it can be seen that there has been brought to the art a new computed tomography scanning system 10. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

What is claimed is:

1. An imaging system comprising:
   an x-ray source adapted to generate an x-ray flux;
   a first analogic computer module comprising a first detector array, said first analogic computer module adapted to generate a first module signal in response to said x-ray flux, wherein said first analogic computer module comprises a memory unit adapted to store intermediate stages of an image generation cycle from said detector array; and
   a host computer adapted to receive said first module signal.

2. The system of claim 1, wherein said x-ray source comprises an extended x-ray source, or a standard x-ray tube.

3. The system of claim 1, wherein said first analogic computer module comprises a communication unit adapted to send and receive signals from said host computer.

4. The system of claim 1, further comprising a second analogic computer module comprising a second detector array, said second analogic computer module adapted to generate a second module signal in response to said x-ray flux.

5. The system of claim 4, wherein said first analogic computer module is adapted to electrically communicate with said second analogic computer module.

6. A method for data collection for an imaging system comprising:
   activating an x-ray source;
   generating an x-ray flux;
   receiving said x-ray flux in at least one analogic computer module comprising a detector array, a memory unit, and a communication unit;
   storing intermediate stages of an image generation cycle from said x-ray flux in said memory unit;
   generating a module signal in response to said x-ray flux;
   receiving said module signal in a host computer; and
   receiving signals from said host computer in said communication unit.

7. The method of claim 6 further comprising:

generating a three dimensional image of an object;

generating a series of axial slices through said object);

tracking a location of a probe within said object; and displaying probe information obtained from said step of tracking on said three dimensional image.

8. The method of claim 6 further comprising generating a two dimensional image.

9. The method of claim 6 further comprising generating a three dimensional image.

10. A computed tomography system comprising:

an x-ray source adapted to generate an x-ray flux;

first analogic computer module comprising a first detector array, said first analogic computer module adapted to generate a first module signal in response to said x-ray flux, wherein said first analogic computer module comprises a communication unit adapted to send and receive signals from said host computer;

a second analogic computer module comprising a second detector array, said second analogic computer module adapted to electrically communicate with said first analogic computer module, said second analogic computer module further adapted to generate a second module signal in response to said x-ray flux; and a host computer adapted to receive said first module signal and said second module signal.

11. The system of claim 10, wherein said x-ray source comprises an extended area x-ray source, or a standard x-ray tube.

12. The system of claim 10, wherein said first analogic computer module comprises a memory unit adapted to store intermediate stages of an image generation cycle from said detector array.

13. The system of claim 10, wherein said first analogic computer module is adapted to electrically communicate with said second analogic computer module.

14. The system of claim 10, wherein said x-ray source comprises an extended x-ray source, or a standard x-ray tube.

* * * * *